United States Patent [19]

Hawkins

[11] 4,002,655

[45] Jan. 11, 1977

[54] GLYCYRRHETINIC ACID DERIVATIVES

[75] Inventor: David William Hawkins, Pinner, England

[73] Assignee: Biorex Laboratories Limited, London, England

[22] Filed: Feb. 10, 1975

[21] Appl. No.: 548,767

[30] Foreign Application Priority Data

Feb. 8, 1974 United Kingdom ............... 5817/74

[52] U.S. Cl. ...................... 260/404.5; 260/482 P; 260/485 H; 260/489; 260/559 S; 424/311; 424/312; 424/313; 424/324

[51] Int. Cl.² ....................... C07C 103/28

[58] Field of Search ............ 260/489, 490, 404.5, 260/485 H, 559 S

[56] References Cited

UNITED STATES PATENTS

| 3,412,084 | 11/1968 | Turner et al. | 260/488 B |
|---|---|---|---|
| 3,734,944 | 5/1972 | Turner | 260/488 B |
| 3,810,927 | 5/1974 | Boran et al. | 260/488 B |

Primary Examiner—Vivian Garner
Attorney, Agent, or Firm—Wenderoth, Lind & Ponack

[57] ABSTRACT

The present invention provides new and pharmaceutically useful amides of the general formula:

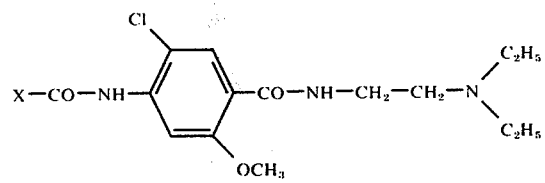

wherein X is the acyl residue of 18α- or 18β-glycyrrhetinic acid, the 3-hydroxyl group of which can be acylated with a mono-, di- or polybasic inorganic or organic acid, or X is the acyl residue of 3-keto-18α- or 18β-glycyrrhetinic acid; and the metoclopramide salts of those compounds containing at least one free carboxylic acid group.

6 Claims, No Drawings

GLYCYRRHETINIC ACID DERIVATIVES

BACKGROUND OF THE INVENTION

U.S. Patent No. 3,412,084 describes and claims, inter alia, compounds of the general formula:-

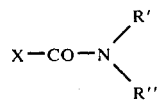

wherein R' can be a hydrogen atom, R" can be a substituted alkyl radical and X can be the acyl residue of 18α- or 18β- glycyrrhetinic acid, the 3-hydroxyl group of which can be acylated with a mono- or polycarboxylic acid or X can be the acyl residue of 3-keto-18α- or -18β-glycyrrhetinic acid. These compounds have an excellent anti-inflammatory activity and a low toxicity.

According to the present invention, we have now found a special group of compounds which are particularly useful for the treatment of disorders of the gastrointestinal tract.

SUMMARY OF THE INVENTION

Thus, the present invention provides amides derived from glycyrrhetinic acid and glycyrrhetinic acid derivatives containing at least one free acid group and metoclopramide, i.e., 4-amino-5-chloro-N-[2-(diethylamino)-ethyl]-o-anisamide, which has the following structural formula:-

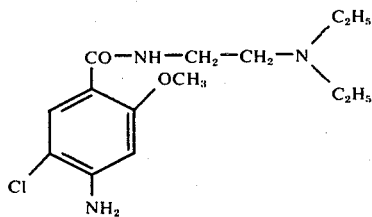

DETAILED DESCRIPTION OF THE INVENTION

The new compounds according to the present invention are of the amides formed by the reaction between the primary amine group of metoclopramide and glycyrrhetinic acid, 3-keto-glycyrrhetinic acid and glycyrrhetinic acid, the 3-hydroxyl group of which is acylated by a mono-, di- or polybasic inorganic or organic acid.

The 3-hydroxyl group of the glycyrrhetinic acid residue is preferably acylated with a mono- or dicarboxylic acid containing up to 20 and preferably up to 12 carbon atoms, for example, with acetic, propionic, butyric, lauric, oleic, stearic, succinic or glutamic acid.

The preferred compounds according to the present invention are derivatives of glycyrrhetinic acid and glycyrrhetinic acid hemisuccinate, this latter compound being described and claimed in our British Patent Specification No. 843,133.

For the preparation of the new amides according to the present invention, the 3-hydroxyl group of glycyrrhetinic acid is acylated with a monocarboxylic acid, the free carboxylic acid group is converted into an acid halide group and the compound thus obtained then reacted with metoclopramide, whereafter, if desired, the acyl radical in the 3-position is removed by hydrolysis, the liberated 3-hydroxyl group thereafter, if desired, either oxidised to give a 3-keto group or acylated with a mono-, di- or polybasic acid and, when a di- or polybasic acid has been used, the free acid group or groups is or are, if desired, reacted with a further amount of metoclopramide to bring about salt formation.

The following Examples are given for the purpose of illustrating the present invention:

EXAMPLE 1

9.0 g. metoclopramide was stirred in 130 ml. dry tetrahydrofuran and 1.44 g. (50% in oil) sodium hydride was added in portions, under an atmosphere of oxygen-free nitrogen. The solution thus obtained was refluxed for 1 hour to give a yellow suspension which was cooled to 0° C. with an ice-salt mixture. A solution of 5.31 g. 3β-O-acetyl-18β-glycyrrhetoyl chloride in 100 ml. dry tetrahydrofuran was then added dropwise and the reaction mixture then stirred for about 6 hours (monitored by thin layer chromatography, solvent chloroform-methanol (85:15)). Thereafter, the reaction mixture was poured into dilute hydrochloric acid and extracted with chloroform. The chloroform layer was washed with dilute hydrochloric acid to remove unreacted metoclopramide and then washed with aqueous sodium bicarbonate solution and water, dried over anhydrous sodium sulphate and evaporated. The residue obtained was taken up in chloroform-methanol and excess diazomethane added thereto, while cooling in an ice-water bath. When the excess 3β-O-acetyl-18β-glycyrrhetinic acid has been converted into methyl 3β-O-acetyl-18β-glycyrrhetate (monitored by thin layer chromatography, solvent chloroformmethanol (85:15)), acetic acid was added dropwise to destroy unreacted diazomethane and the solution then evaporated to dryness. Trituration with petroleum either (b.p. 40° – 60° C.) gave, upon filtration, 7.5 g. of crude amide. This was chromatographed on 200 g. of silica gel MFC and eluted with petroleum ether/ethyl acetate (4:1) to give methyl 3β-O-acetyl-18β-glycyrrhetate, which was discarded. Further elution with ethyl acetate/ethanol (4:1) gave the desired N-(3β-O-acetyl-18β-glycyrrhetyl)-4-amino-5-chloro-N'-(2-diethylaminoethyl)-2-methoxy-benzamide, together with a small amount of the corresponding 3-hydroxy compound. Crystallisation of the desired amide gave 2.1 g. of pure product (over 99% purity), which had a melting point of 226° – 228° C.

EXAMPLE 2

500 mg. N-(3β-O-acetyl-18β-glycyrrhetyl)-4-amino-5-chloro-N'-(2-diethylaminoethyl)-2-methoxy-benzamide (see Example 1) were dissolved in 20 ml. methanol and treated with a solution of 1 g. potassium hydroxide in 30 ml. methanol at ambient temperature. After 30 hours, the reaction mixture was poured into water and extracted twice with chloroform. The organic phase was washed with water until neutral, dried over anhydrous sodium sulphate and evaporated. The evaporation residue was triturated with petroleum ether/diethyl ether to give 470 mg. N-(18β-glycyrrhetyl)4-amino-5-chloro-N'-(2-diethylaminoethyl)-2-methoxy-benzamide which, after recrystallisation from acetone, melted with decomposition at 242° – 245° C.; [α]$_D$ = + 159.5° ± 2° (c. = 1% in chloroform).

EXAMPLE 3

1.835 g. metoclopramide was dissolved in 250 ml. dry tetrahydrofuran (freshly distilled from lithium aluminium hydride) and stirred, while refluxing under argon, with 325 mg. sodium hydride (50% dispersion). After 1 hour, the yellow suspension was cooled in an icebath and a solution of 1.37 g. 3β-O-lauroyl-18β-glycyrrhetoyl chloride in 20 ml. dry tetrahydrofuran added dropwise over the course of 20 minutes. The reaction was stirred and allowed to reach ambient temperature before leaving to stand overnight. The reaction mixture was then carefully poured into 2N hydrochloric acid and extracted with chloroform. The organic phase was extracted three times with 2N hydrochloric acid to remove unreacted metoclopramide as its hydrochloride. The chloroform solution was then washed with an aqueous solution of sodium bicarbonate until alkaline and then once with water and subsequently dried over anhydrous sodium sulphate and evaporated in a vacuum. The crude product thus obtained was dissolved in 40 ml. chloroform/methanol and treated with an excess of an ethereal solution of diazomethane to convert the major impurity, i.e., 3β-O-lauroyl-18β-glycyrrhetinic acid, into the corresponding methyl ester. The solution was evaporated and chromatographed on 80 g. alumina MFC, elution being carried out with ethyl acetate/petroleum ether (3:7). Evaporation of the eluate gave an oil which was triturated with petroleum ether to give 520 mg. of a white solid, recrystallisation of which from methanol gave pure N-(3β-O-lauroyl-18β-glycyrrhetyl)-4-amino-5-chloro-N'-(2-diethylaminoethyl)-2-methoxy-benzamide, which melted at 148.5° – 152° C.; $[\alpha]_D = +142° \pm 2°$ (c. = 1% in chloroform).

The 3β-O-lauroyl-18β-glycyrrhetoyl chloride used as starting material is prepared as follows:

3.0 g. 3β-O-lauroyl-18β-glycyrrhetinic acid were refluxed for 1 hour with 10 ml. thionyl chloride, whereafter excess thionyl chloride was distilled off in a vacuum. 20 ml. dry toluene were then added and vacuum distillation continued to remove traces of thionyl chloride and until solidification occurred. The addition of the minimum amount of petroleum ether (b.p. 60° – 80° C.) resulted in crystallisation of the 3β-O-lauroyl-18β-glycyrrhetoyl chloride, which was filtered off and dried at 70° C.

EXAMPLE 4

100 mg. N-(18β-glycyrrhetyl)-4-amino-5-chloro-N'-(2-diethylaminoethyl)-2-methoxy-benzamide (see Example 2) were dissolved in 4 ml. of Cornforth's reagent (a solution of chromium trioxide in aqueous pyridine) and left to stand at ambient temperature for 16 hours. The dark-coloured reaction mixture was poured into 2N hydrochloric acid and extracted with chloroform. The organic phase was wahsed twice with 2N hydrochloric acid, once with water and once with aqueous sodium bicarbonate solution, then dried over anhydrous sodium sulphate and evaporated. The residue was purified by chromatography and triturated with diethyl ether/petroleum ether to give N-(3-keto-18β-glycyrrhetyl)-4-amino-5-chloro-N'-(2-diethylaminoethyl)-2-methoxy-benzamide, which melted at 222.5° – 225° C.; $[\alpha]_D = +188° \pm 5°$ (c. = 1% in chloroform).

EXAMPLE 5

3 g. N-(18β-glycyrrhetyl)-4-amino-5-chloro-N'-(2-diethylaminoethyl)-2-methoxy-benzamide in 10 ml. dry pyridine were heated with 1.192 g. succinic anhydride under an atmosphere of argon at an external temperature of 115° – 120° C. After 8 hours, the dark-coloured solution was allowed to cool. Excess water was then added and the suspension obtained was heated on a steambath for 30 minutes. The brown solid obtained was filtered off, washed with water and dissolved in chloroform. This solution was washed twice with water, dried over anhydrous sodium sulphate and evaporated in a vacuum. The evaporation residue was recrystallised three times from chloroformmethanol, with the use of decolorising charcoal, to give 2.08 g. pure N-[3β-O-(γ-carboxypropionyl)-18β-glycyrrhetyl]-4-amino-5-chloro-N'-(2-diethylaminoethyl)-2-methoxy-benzamide which melted, with decomposition, at 254° – 256.5° C.; $[\alpha]_D = +129.2°$ (c. = 1% in chloroform).

The present invention also includes within its scope pharmaceutical compositions containing at least one of the new compounds, in admixture with a solid or liquid pharmaceutical carrier, which can be administered orally or parenterally.

Solid compositions for oral administration include compressed tablets, pills, dispersible powders and granules. In such solid compositions, one of the new esters is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents, and sweetening and flavouring agents.

The compositions according to the present invention for oral administration, include capsules of absorbable material, such as gelatine, containing one of the new compounds, with or without the addition of diluents or excipients.

Preparations according to the present invention for parenteral administration include sterile aqueous or nonaqueous solutions, suspensions or emulsions. Examples of non-aqueous solvents or suspending media include propylene glycol, polyethylene glycol, vegetable oils, such as olive oil, and injectable organic esters, such as ethyl oleate. These compositons may also contain adjuvants, such as wetting, emulsifying and dispersing agents. They may be sterilised, for example, by filtration through bacteria-retaining filters, by incorporation into the compositions of sterilising agents, by irradiation or by heating. They may also be produced in the form of sterile solid compositions, which can be dissolved in sterile water or some other sterile injectable medium immediately before use.

The percentage of active material in the compositions of the present invention may be varied, it being necessary that it should constitute a proportion such that a suitable dosage for the desired therapeutic effect shall be obtained. In general, the preparations of the present invention should be administered orally or parenterally to humans to give 10 to 1000 mg., preferably 50 – 500 mg. of active substance per day.

The following Examples illustrate pharmaceutical compositions according to the present invention:

EXAMPLE 6

Example 6

| 250 mg. tablets are prepared containing: | |
|---|---|
| N-(18β-glycyrrhetyl)-4-amino-5-chloro-N'-(2-diethylaminoethyl)-2-methoxy-benzamide | 50 mg. |
| starch | 100 mg. |
| lactose | 95 mg. |
| magnesium stearate | 5 mg. |

EXAMPLE 7

Example 7

| 400 mg. tablets are prepared containing: | |
|---|---|
| N-[3β-o-(γ-carboxypropionyl)-18β-glycyrrhetyl]-4-amino-5-chloro-N'-(2-diethylaminoethyl)-2-methoxy-benzamide | 100 mg. |
| starch | 130 mg. |
| lactose | 160 mg. |
| magnesium stearate | 10 mg. |

The compositions according to Examples 6 and 7 are intended for oral administration to humans for the treatment of inflammatory conditions of the gastrointestinal tract and especially of the stomach.

I claim:

1. A compound selected from the group consisting of compounds of the formula

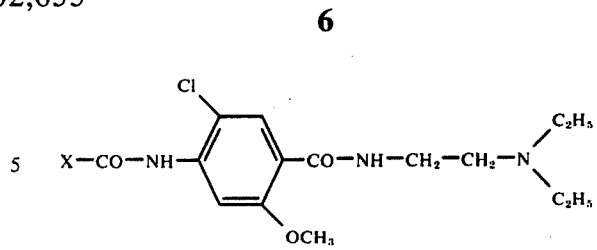

wherein X is the acyl residue of 18α- or 18β-glycyrrhetinic acid, the 3-hydroxyl group of which is optionally acylated with a monobasic fatty acid containing up to 20 carbon atoms or succinic acid and the metoclopramide salt of said compound wherein the 3-hydroxy group is acylated with succinic acid.

2. A compound according to claim 1, wherein X is the acyl residue of 18α- or 18β-glycyrrhetinic acid, the 3-hydroxyl group of which is optionally acylated with a monobasic fatty acid containing up to 20 carbon atoms or succinic acid.

3. The compound according to claim 1, which is N-(3β-O-acetyl-18β-glycyrrhetyl)-4-amino-5-chloro-N'-(2-diethylaminoethyl)-2-methoxy-benzamide.

4. The compound according to claim 1, which is N-(18β-glycyrrhetyl)-4-amino-5-chloro-N'-(2-diethylaminoethyl)-2-methoxy-benzamide.

5. The compound according to claim 1, which is N-(3β-O-lauroyl-18β-glycyrrhetyl)-4-amino-5-chloro-N'-(2-diethylaminoethyl)-2-methoxy-benzamide.

6. The compound according to claim 1, which is N-[3β-O-(γ-carboxypropionyl)-18β-glycyrrhetyl]-4-amino-5-chloro-N'-(2-diethylaminoethyl)-2-methoxy-benzamide.

* * * * *